(12) United States Patent
Courtney et al.

(10) Patent No.: US 9,480,805 B2
(45) Date of Patent: Nov. 1, 2016

(54) MATERIAL RECOVERY AND CAPTURE DEVICE FOR ATOMIZED MATERIAL DELIVERY APPARATUSES

(71) Applicants: Lloyd Courtney, Salinas, CA (US); Ann Louise Yant, Salinas, CA (US)

(72) Inventors: Lloyd Courtney, Salinas, CA (US); Ann Louise Yant, Salinas, CA (US)

(73) Assignees: Lloyd Courtney, Salinas, CA (US); Ann Louise Yant, Salinas, CA (US)

( * ) Notice: Subject to any disclaimer, the term of this patent is extended or adjusted under 35 U.S.C. 154(b) by 59 days.

(21) Appl. No.: 14/546,558

(22) Filed: Nov. 18, 2014

(65) Prior Publication Data

US 2015/0224271 A1  Aug. 13, 2015

Related U.S. Application Data

(60) Provisional application No. 61/965,937, filed on Feb. 11, 2014.

(51) Int. Cl.
*A61M 16/14* (2006.01)
*A61M 16/20* (2006.01)
(Continued)

(52) U.S. Cl.
CPC ............ *A61M 16/009* (2013.01); *A61M 11/00* (2013.01); *A61M 15/0021* (2014.02); *A61M 16/0816* (2013.01); *A61M 16/14* (2013.01); *A61M 16/208* (2013.01); *A61M 2202/0208* (2013.01)

(58) Field of Classification Search
CPC . A61B 5/0813; A61M 11/002; A61M 11/06; A61M 15/0015; A61M 15/0016; A61M 15/0018; A61M 15/0021; A61M 15/0085; A61M 15/0086; A61M 15/0088; A61M 15/009; A61M 16/009; A61M 16/0093; A61M 16/06; A61M 16/08; A61M 16/1045; A61M 16/22; A61M 2205/75; Y10S 128/909; Y10S 128/91
USPC ............ 128/200.14, 200.16, 200.18, 200.21, 128/200.22, 200.24, 201.13, 202.27, 128/203.12, 203.23, 203.28, 204.18, 128/204.25, 205.12, 205.24, 205.29, 909, 128/910
See application file for complete search history.

(56) References Cited

U.S. PATENT DOCUMENTS 3,561,444 A * 2/1971 Boucher ........... A61M 15/0085
128/200.16
4,007,737 A * 2/1977 Paluch .................. A61M 16/06
128/201.13

(Continued)

FOREIGN PATENT DOCUMENTS

EP 1927373 6/2008
GB 2131702 A 6/1984

OTHER PUBLICATIONS

International Search Report and Written Opinion for PCT/US2015/013590 dated May 8, 2015, 11 pgs.

*Primary Examiner* — Annette Dixon
(74) *Attorney, Agent, or Firm* — Procopio, Cory, Hargreaves & Savitch LLP

(57) ABSTRACT

A recovery and collection assembly for an atomized material inhalation device is provided. The recovery and collection assembly includes an outer tubular housing and an input tube. The outer tubular housing includes a sidewall defining an outer chamber, an upper end piece attached to an upper end of the sidewall, and a lower end piece attached to a lower end of the sidewall. The lower end piece has at least one air flow opening allowing fluid communication between an interior of the outer chamber and an atmosphere surrounding the outer tubular housing. The input tube extends through the lower end piece and has a first end in fluid communication with the atomized material inhalation device. The input tube also has a second end disposed in an upper half of the outer chamber and in fluid communication with the outer chamber and defines an inner chamber.

12 Claims, 17 Drawing Sheets

(51) Int. Cl.
*A61M 16/00* (2006.01)
*A61M 11/00* (2006.01)
*A61M 16/08* (2006.01)
*A61M 15/00* (2006.01)

(56) References Cited

U.S. PATENT DOCUMENTS

| | | | |
|---|---|---|---|
| 4,094,317 A | 6/1978 | Wasnich | |
| 4,265,235 A * | 5/1981 | Fukunaga | A61M 16/08 128/200.24 |
| 4,333,451 A * | 6/1982 | Paluch | A61M 16/0808 128/205.12 |
| 4,463,755 A * | 8/1984 | Suzuki | A61M 16/08 128/200.18 |
| 5,284,160 A * | 2/1994 | Dryden | A61M 16/08 128/203.12 |
| 5,584,285 A * | 12/1996 | Salter | A61M 11/06 128/200.21 |
| 5,603,314 A | 2/1997 | Bono | |
| 5,613,489 A | 3/1997 | Miller et al. | |
| 5,901,705 A * | 5/1999 | Leagre | A61M 16/08 128/204.17 |
| 6,129,082 A * | 10/2000 | Leagre | A61M 16/08 128/205.27 |
| 6,230,703 B1 | 5/2001 | Bono | |
| 6,363,932 B1 * | 4/2002 | Forchione | A61M 15/0086 128/200.14 |
| 6,578,571 B1 | 6/2003 | Watt | |
| 6,595,203 B1 | 7/2003 | Bird | |
| 7,178,521 B2 * | 2/2007 | Burrow | A61M 16/0816 128/202.27 |
| 7,267,120 B2 | 9/2007 | Rustad et al. | |
| 7,270,123 B2 | 9/2007 | Grychowski et al. | |
| 7,418,962 B1 | 9/2008 | Rao | |
| 2001/0047804 A1 * | 12/2001 | Fukunaga | A61M 16/1055 128/205.27 |
| 2010/0065053 A1 | 3/2010 | Haveri | |
| 2013/0061849 A1 | 3/2013 | Lemper | |

* cited by examiner

MATERIAL RECOVERY AND CAPTURE DEVICE FOR ATOMIZED MATERIAL DELIVERY APPARATUSES

CROSS-REFERENCE TO RELATED APPLICATIONS

This application claims benefit of priority from Provisional U.S. patent application Ser. No. 61/965,937, filed Feb. 11, 2014, the contents of which are incorporated by reference.

TECHNICAL FIELD

The present disclosure relates generally to nebulizers for inhalation of atomized materials, and more specifically to systems and methods for recovering material during administration of atomized materials using a nebulizer.

BACKGROUND

Related art nebulizers, or other aerosol medication delivery apparatuses, provide a constant flow of atomized materials during normal operation. However, the user of a nebulizer can only take in the atomized materials during inhalation. During the user's exhalation, the related art nebulizers continue to provide atomized materials, but these materials are lost to the atmosphere when they are not inhaled by the user.

For example, during a normal respiration cycle, about 50% of the time may be spent inhaling and about 50% of the time may be spent exhaling. Depending on the material being provided in the related art nebulizers, this material lost to the atmosphere can represent a significant waste of material and money. For example, some medications provided via related art nebulizers can cost upwards of $250 per dose and a patient may be on a treatment protocol receiving multiple doses each day, over a course of months or years. If up to 50% of the medicine is being lost when every dose is being administered, thousands of dollars of wasted medicine may be lost to the atmosphere each year.

SUMMARY

Aspects of the example implementations may be directed to methods and systems to collect and recover atomized materials during non-inhalation phases of nebulizer treatments.

Aspects of the present application may include a recovery and collection assembly. The recovery and collection assembly includes an outer tubular housing and an input tube. The outer tubular housing includes a sidewall defining an outer chamber, an upper end piece attached to an upper end of the sidewall, and a lower end piece attached to a lower end of the sidewall. The lower end piece has at least one air flow opening allowing fluid communication between an interior of the outer chamber and an atmosphere surrounding the outer tubular housing. The input tube extends through the lower end piece and has a first end in fluid communication with the atomized material inhalation device. The input tube also has a second end disposed in an upper half of the outer chamber and in fluid communication with the outer chamber and defines an inner chamber.

Aspects of the present application may also include an atomized material inhalation device. The atomized material inhalation device may include a material chamber, an air source, a flow passage connecting the air source to the material chamber; and a recovery and collection assembly. The recover and collection assembly includes an outer tubular housing and an input tube. The outer tubular housing includes a sidewall defining an outer chamber, an upper end piece attached to an upper end of the sidewall, and a lower end piece attached to a lower end of the sidewall. The lower end piece has at least one air flow opening allowing fluid communication between an interior of the outer chamber and an atmosphere surrounding the outer tubular housing. The input tube extends through the lower end piece and has a first end in fluid communication with the material chamber. The input tube also has a second end disposed in an upper half of the outer chamber and is in fluid communication with the outer chamber and the input tube defines an inner chamber.

BRIEF DESCRIPTION OF THE DRAWINGS

A general structure that implements the various features of the disclosure will now be described with reference to the drawings. The drawings and the associated descriptions are provided to illustrate example implementations of the disclosure and not to limit the scope of the disclosure. Throughout the drawings, reference numbers are reused to indicate correspondence between referenced elements.

DETAILED DESCRIPTION

The subject matter described herein is taught by way of example implementations. Various details have been omitted for the sake of clarity and to avoid scaring the subject matter.

The example shown below are directed to structures and functions for implementing systems and methods for recovering material during administration of atomized materials using atomized material inhalation devices such as nebulizers. Some example implementations may be directed to recovery and collection assemblies for use with atomized material inhalation devices (e.g. nebulizers) to store the atomized materials produced by the nebulizer during user exhalation. When the user next inhales the user may receive atomized materials recovering collected in the assembly plus new material provided by the nebulizer.

Figure 1:
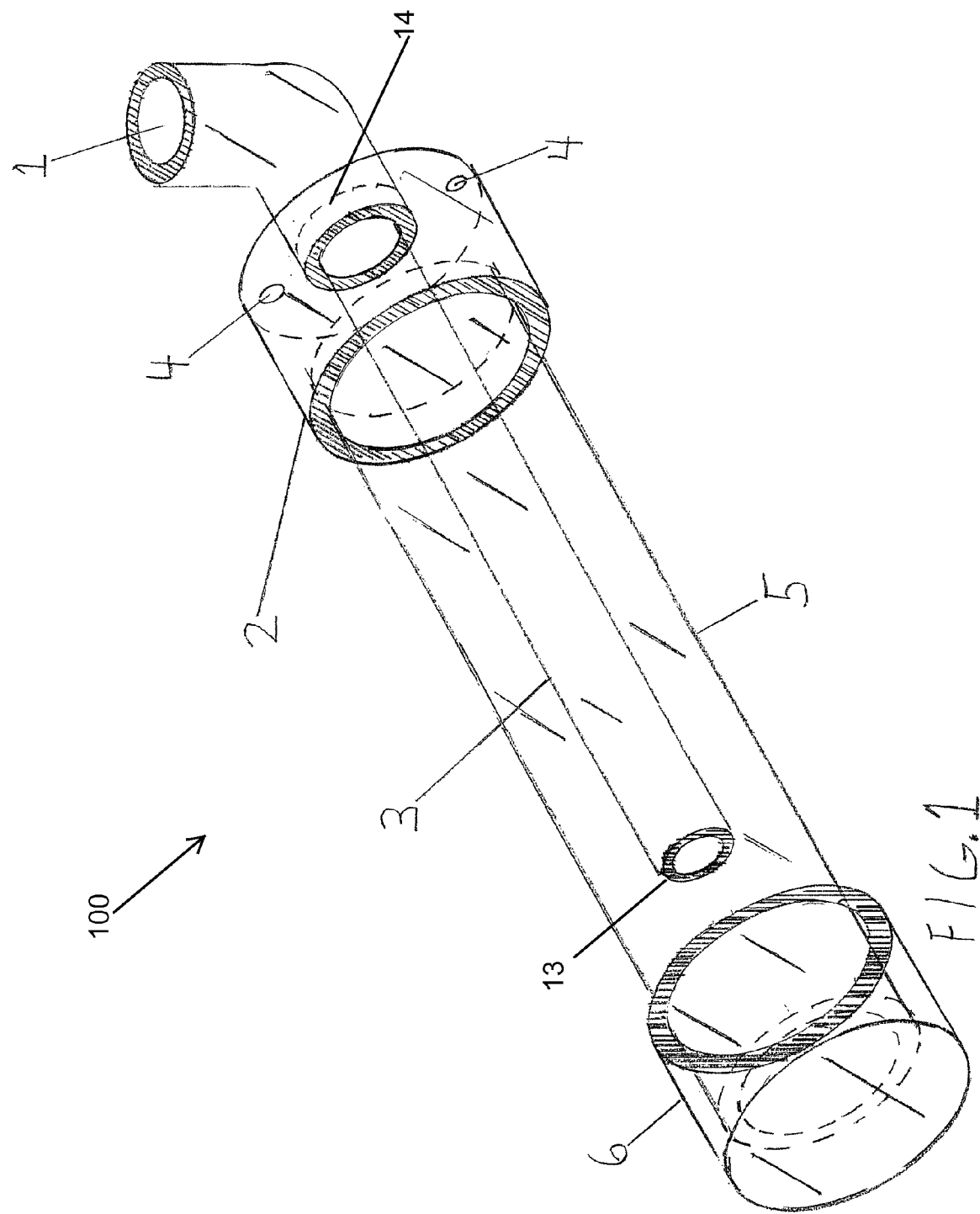
FIG. 1 is a perspective view illustrating a first example implementation of the recovery and collection assembly.
Figure 2:
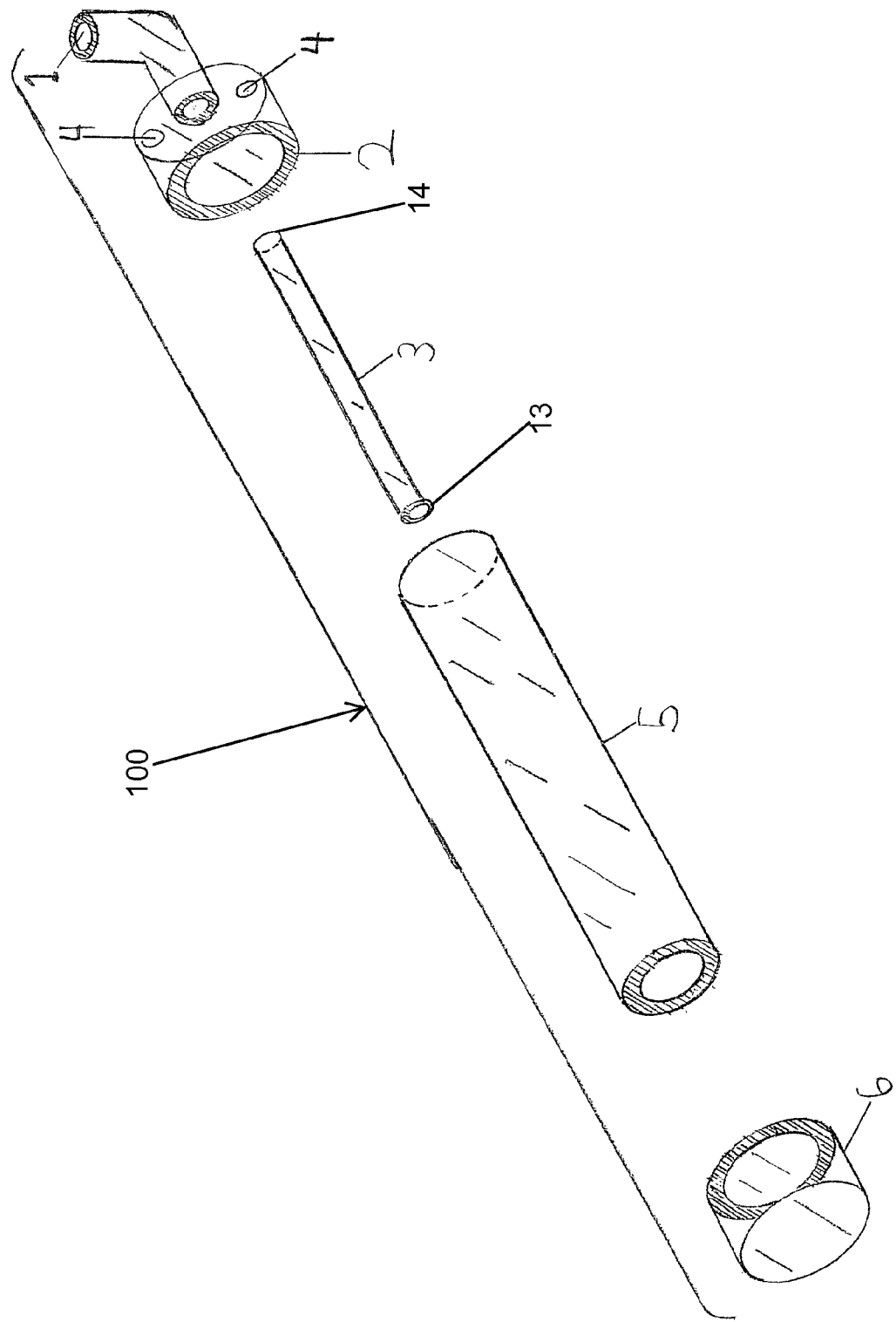
FIG. 2 is an exploded view illustrating the first example implementation of the recovery and collection assembly.

FIG. 1 is a perspective view illustrating a first example implementation of the recovery and collection assembly 100. FIG. 2 is an exploded view illustrating the first example implementation of the recovery and collection assembly 100. The recovery and collection assembly 100 includes an outer tubular housing formed by a tubular sidewall 5 and a pair of end caps or end pieces 2, 6 attach at opposite ends of the tubular sidewall 5. As illustrated in FIG. 1, the end pieces 2, 6 may slide over the ends of the tubular sidewall 5 to form a chamber within the tubular sidewall 5. However, example implementations of the present application are not limited this configuration and may be formed by the end pieces 2, 6 being inserted into the tubular sidewall 5 to form the chamber, or may simply be attached to the end via various attachment mechanisms (such as welding, adhesive, mechanical interface, etc.) as may be apparent to a person of ordinary skill in the art. For reference purposes the chamber formed within the tubular sidewall 5 may be referred to herein as the outer chamber.

In some example implementations, the end pieces 2, 6 may be sealed to the tubular sidewall 5 by one or more of a gasket, an adhesive, a caulking compound, or any other sealing mechanism as may be apparent to a person of ordinary skill in the art to prevent any liquid or gas from leaking out. Further, the end pieces 2, 6 and tubular sidewall 5 may be formed from one or more of a plastic material, a composite material, a resin material, a ceramic material, a glass material, a metallic material, a nonmetallic material, or any other material as may be apparent to a person of ordinary skill in the art.

One end piece 2 may be formed with one or more air flow openings 4 extending there through to allow fluid communications between the area surrounding the recovery and collection assembly 100 and the outer chamber formed within the tubular sidewall 5. The other end piece 6 may be formed with no openings or passageways to block any fluid communication between the area surrounding the recovery and collection assembly 100 and the outer chamber formed within the tubular sidewall 5.

Further, an input tube 3 may be inserted or penetrated through the end piece 2. The input tube 3 may have a first end 13 located within the outer chamber formed by the tubular sidewall 5 and a second end 14 located outside of the outer chamber formed by the tubular sidewall 5. The input tube 3 may form an inner chamber. Further, the second end 14 may be attached to a joint member 1, which may form a connection port configured to fluidly communicate with an atomized material inhalation device (e.g. a nebulizer) as discussed in greater detail below. In some example implementations, the joint member 1 may be an L-shaped elbow joint as illustrated. However, example implementations the present application are not limited to this configuration and may have other configurations as may be apparent to a person of ordinary skill in the art.

In some example implementations, the input tube 3 may be sealed to the end piece 2 by one or more of a gasket, an adhesive, a caulking compound, or any other sealing mechanism as may be apparent to a person of ordinary skill in the art to prevent any liquid or gas from leaking out. Additionally, the joint member 1 may also be sealed to the second end 14 of the input tube 3 using similar sealing mechanisms to those discussed above. The input tube 3 and the joint member 1 may be formed from one or more of a plastic material, a composite material, a resin material, a ceramic material, a glass material, a metallic material, a nonmetallic material, or any other material as may be apparent to a person of ordinary skill in the art.

Figure 3A:
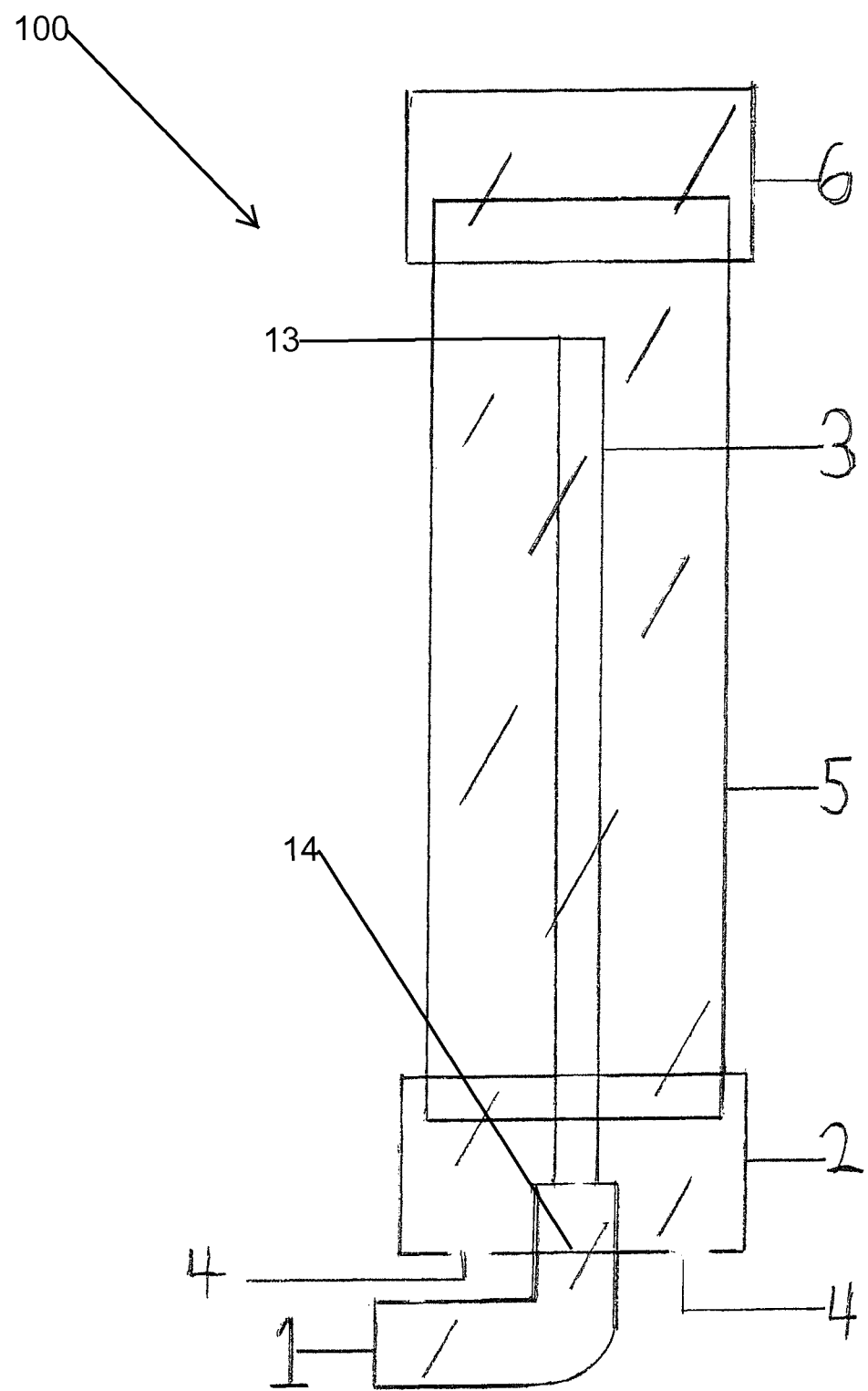
FIGS. 3A and FIG. 3B are side views of the first example implementation of the recovery and collection assembly.
Figure 3B:
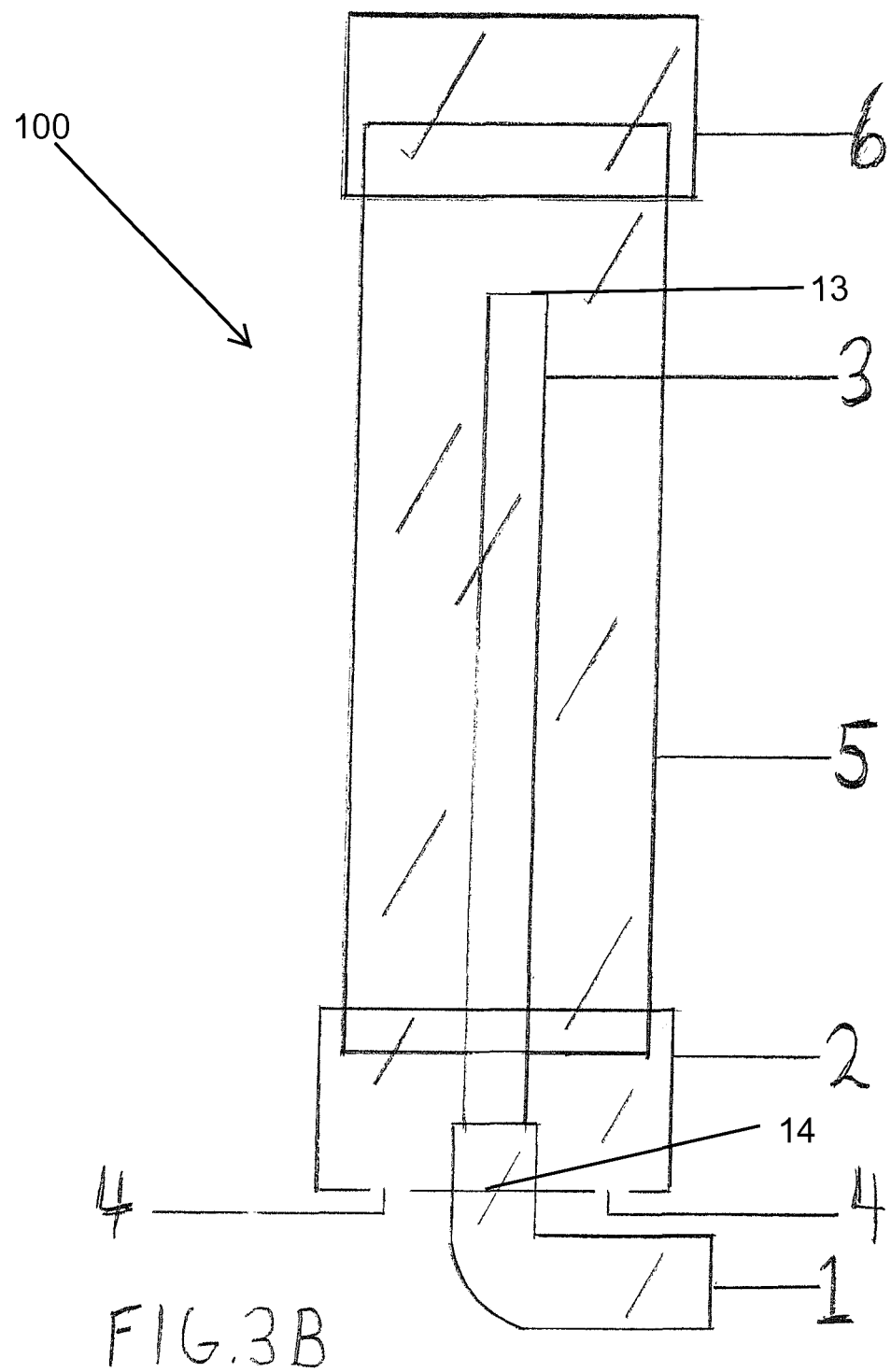
Figure 4A:
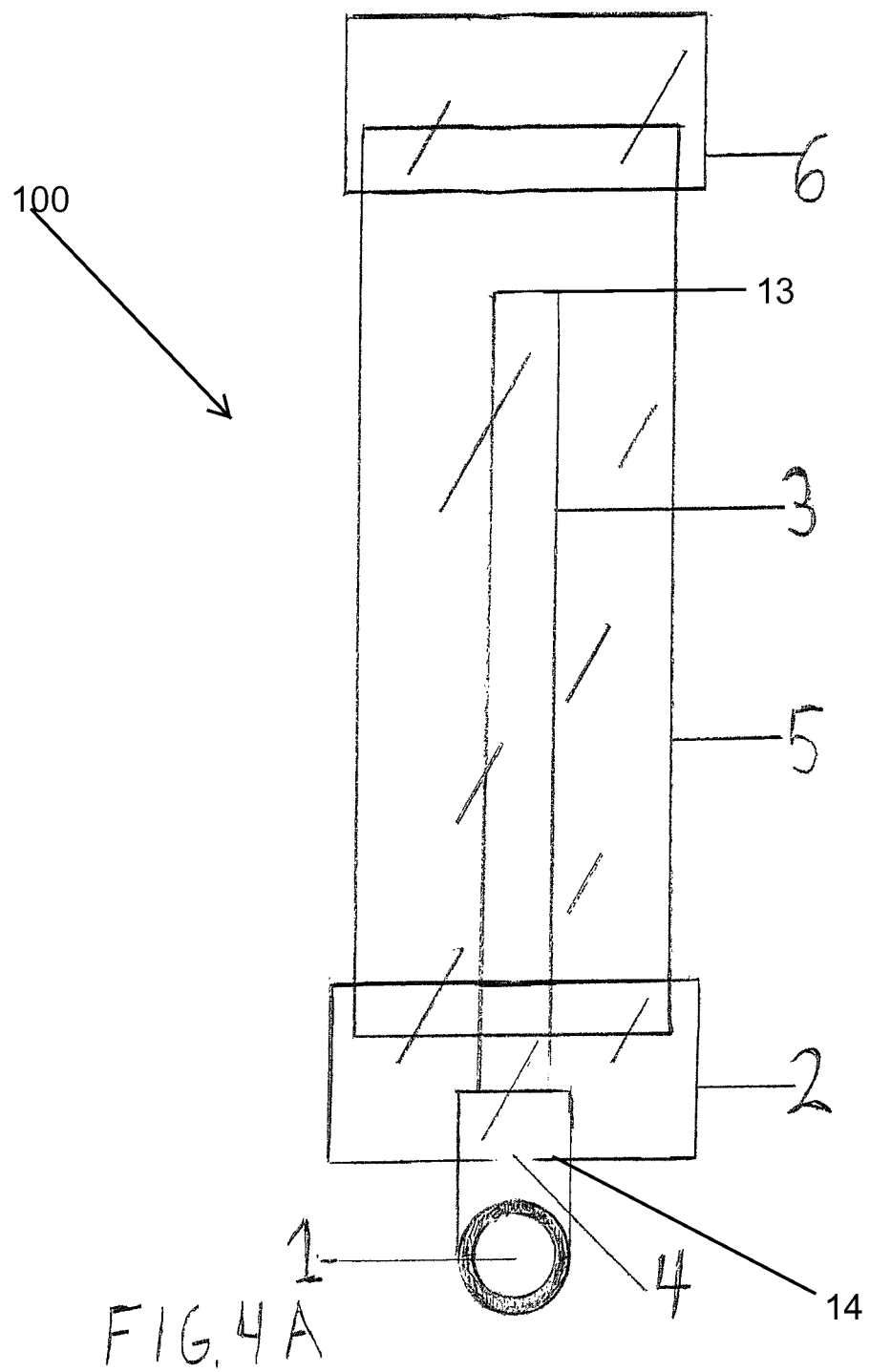
FIGS. 4A and 4B are front and rear views, respectively, of the first example implementation of the recovery and collection assembly.
Figure 4B:
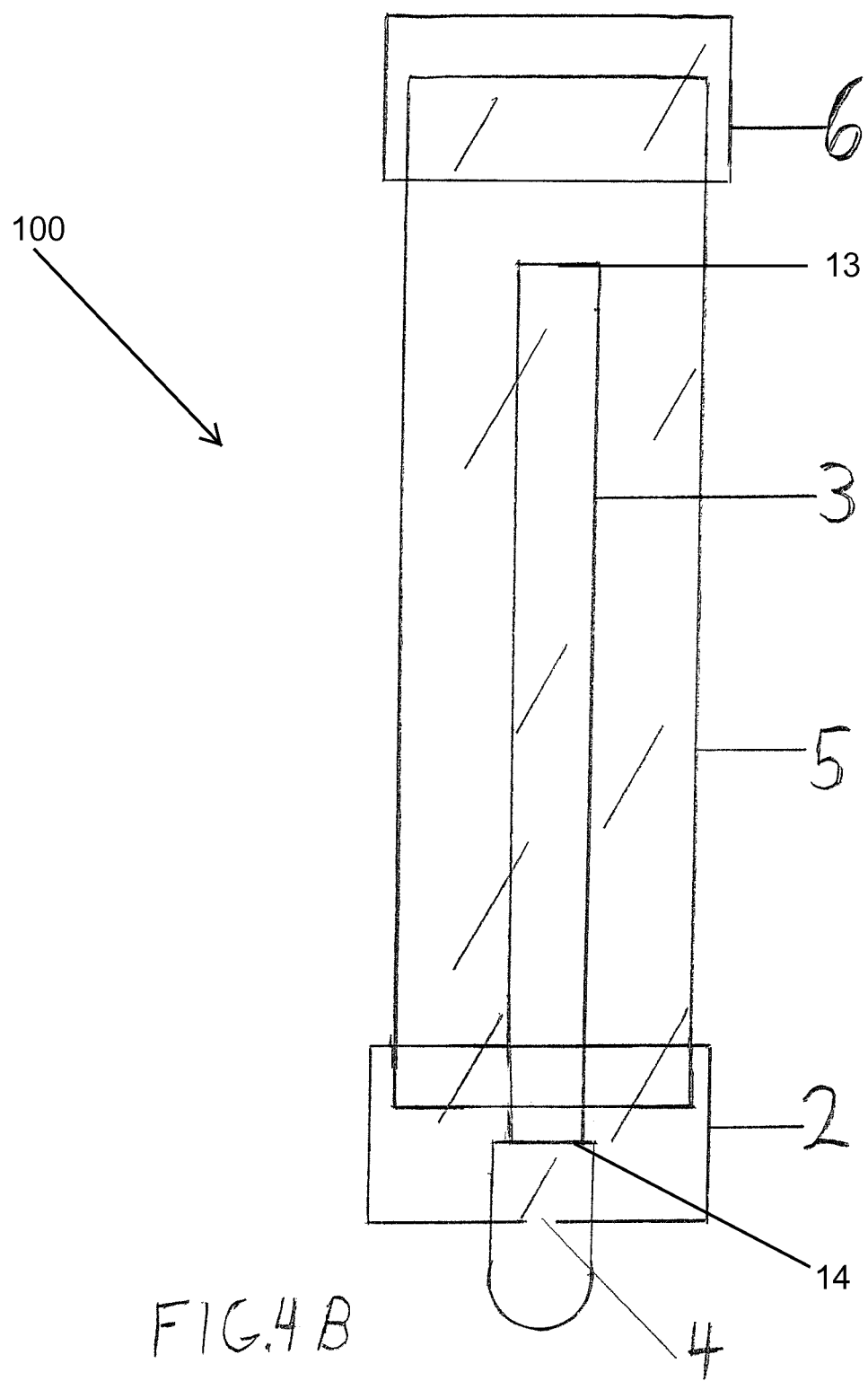

FIG. 3A and FIG. 3B are side views of the first example implementation of the recovery and collection assembly 100. Further, FIG. 4A and 4B are front and rear views, respectively, of the first example implementation of the recovery and collection assembly 100. During operation of some example implementations, the recovery and collection assembly 100 may be oriented such that the end piece 6 is an upper end piece 6 and the end piece 2 is a lower end piece 2 as illustrated in these figures. In such example implementations, the openings 4 are formed in the bottom surface of the lower end piece 2 (end piece). Additionally, the input tube 3 and the joint member 1 may also be inserted through the bottom surface of the lower end piece 2 as illustrated.

Additionally, the first end 13 of the input tube 3 may be positioned so that it is in an upper half of the chamber formed by the tubular sidewall 5. As discussed in greater detail below the placement of the first end 13 in an upper half of the chamber may affect retention of atomized material within the recovery and collection assembly. In some example implementations, the joint member 1 may be in elbow joint oriented to provide a horizontal opening in a forward direction. However, example implementations of the present application are not limited this configuration and may take on alternate configurations as may be apparent to a person of ordinary skill in the art.

Figure 5A:
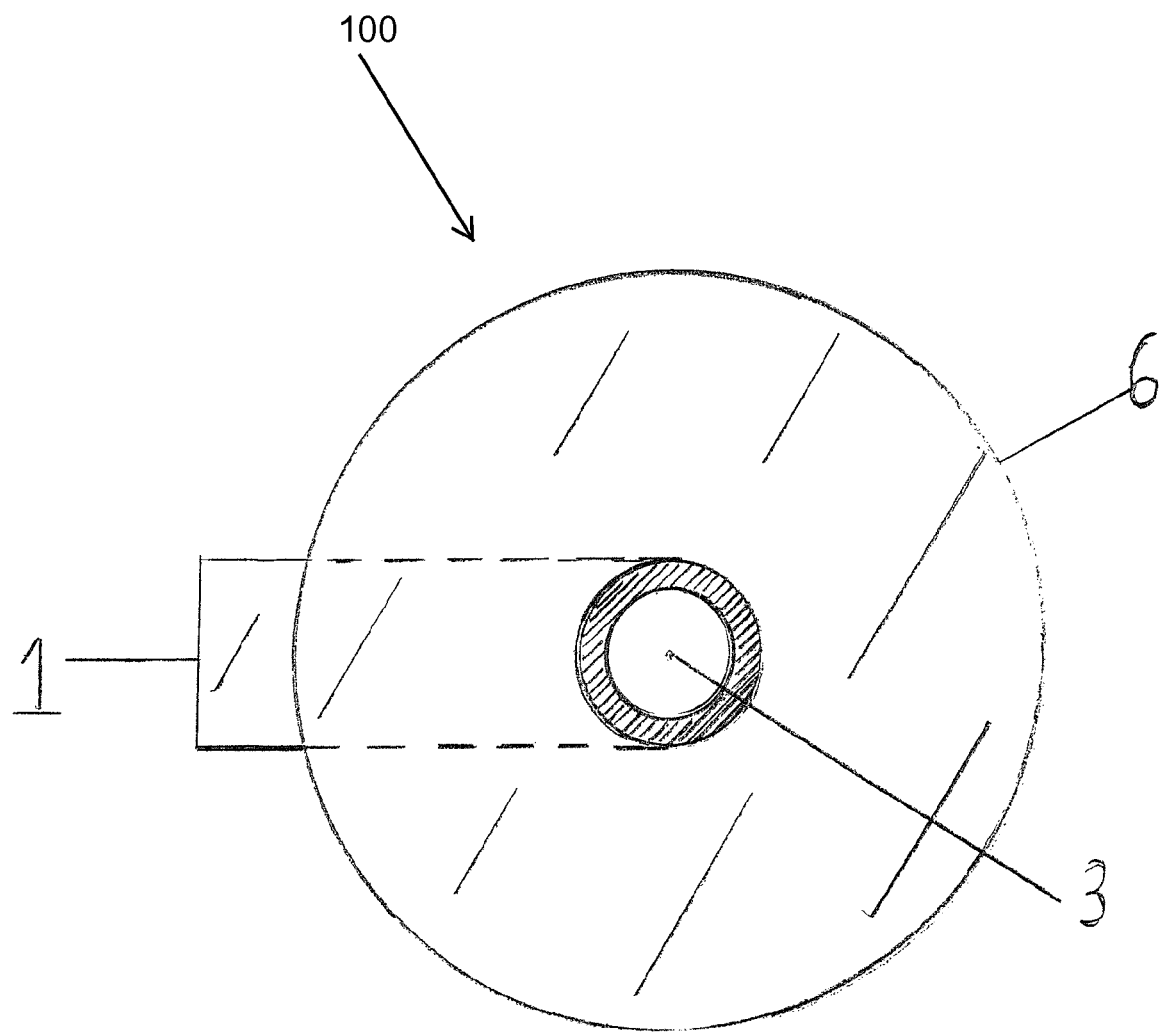
FIGS. 5A and 5B are top and bottom views, respectively, of the first example implementation of the recovery and collection assembly.
Figure 5B:
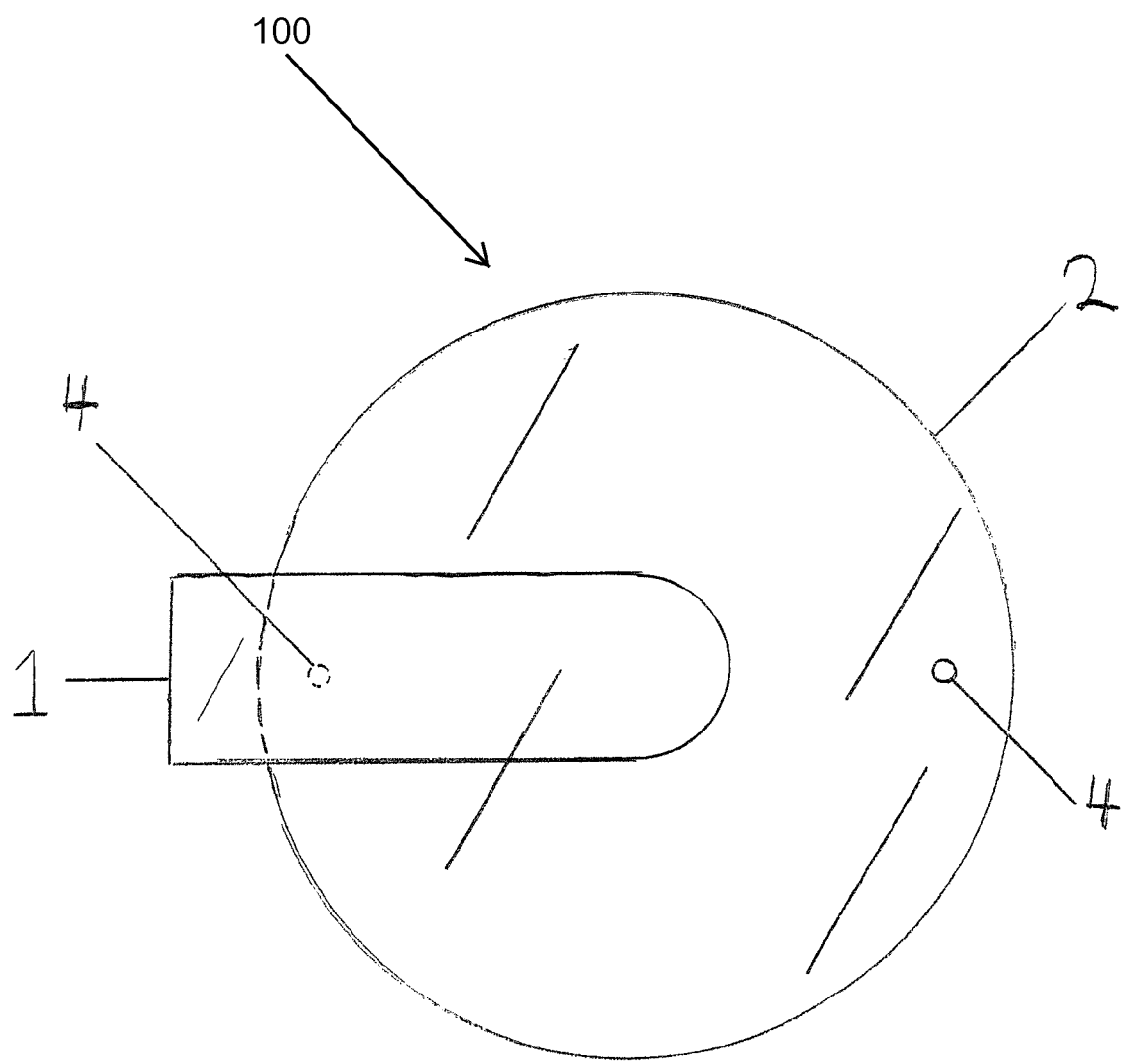

FIG. 5A and 5B are top and bottom views, respectively, of the first example implementation of the recovery and collection assembly 100. As illustrated, the recovery and collection assembly 100 may be formed with a generally circular cross-section. More specifically, the tubular sidewall 5, and the end pieces 2, 6 may have circular cross-sections. Further, the input tube 3 may also have a circular cross-section and be positioned at an approximate radial center of the end pieces 2, 6 and the tubular sidewall 5.

Figure 6:
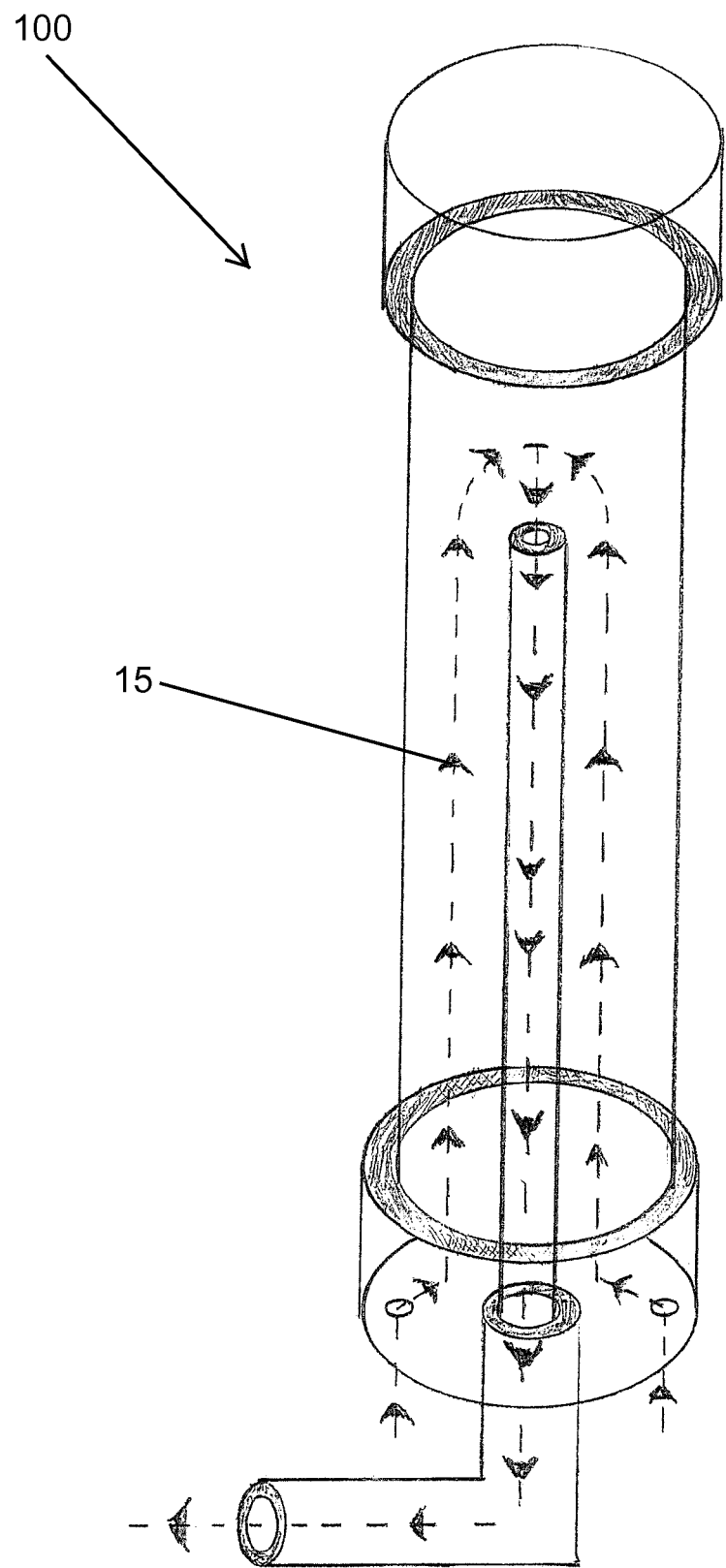
FIG. 6 illustrates an air flow diagram within the first example implementation of the recovery and collection assembly during a user inhalation.

FIG. 6 illustrates an air flow diagram within the first example implementation of the recovery and collection assembly 100 during a user inhalation phase. In FIG. 6, the reference numerals have been removed to aiding visualization of the airflow 15. As illustrated, the airflow 15 travels into the chamber formed by the tubular sidewall 5 through the openings 4 formed in the bottom of the end piece 2. The airflow 15 then travels upward through the chamber formed by the tubular sidewall 5 and enters the upper end 13 of the input tube 3. The airflow 15 then travels downward through the input tube 3, and out of the recovery and collection assembly 100 through the joint member 1 toward the atomized material inhalation device 7 (not illustrated in FIG. 6, illustrated and discussed in greater detail below).

Figure 7:
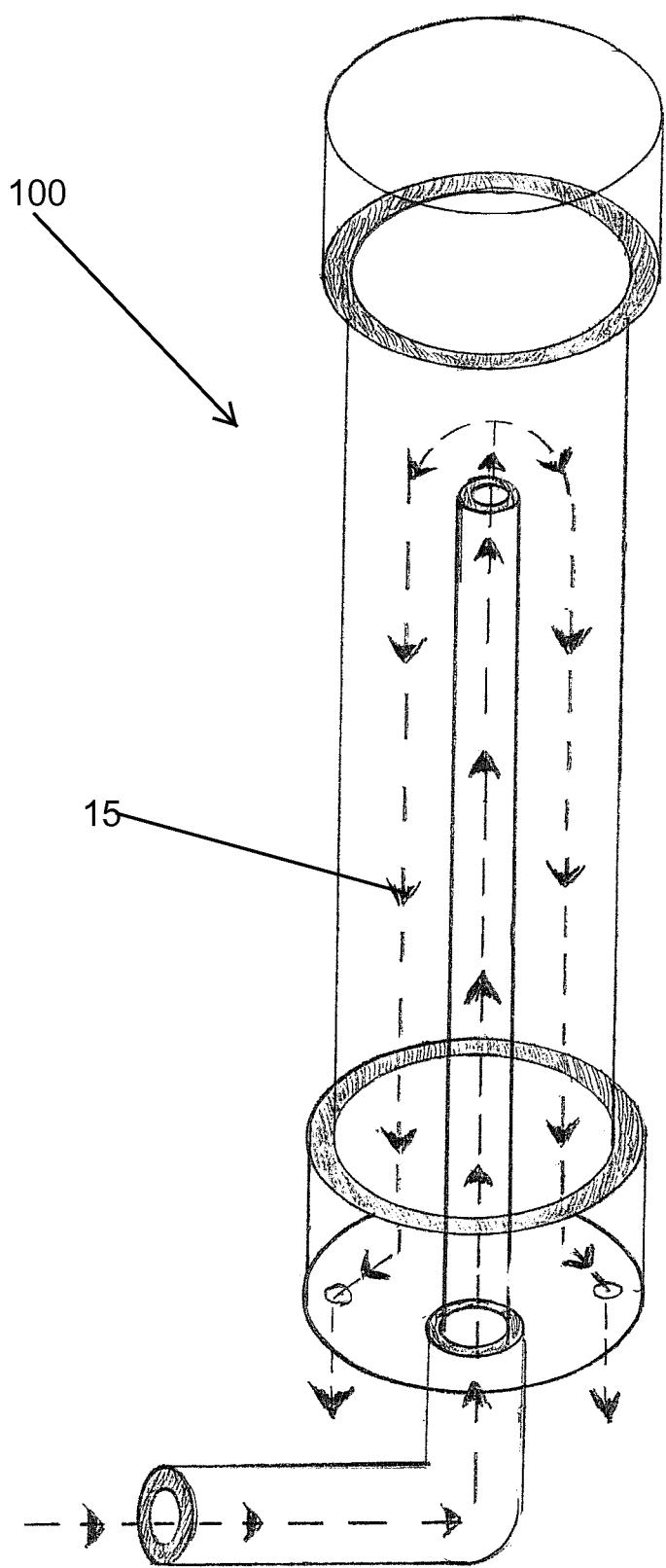
FIG. 7 illustrates an air flow diagram within the first example implementation of the recovery and collection assembly during a user exhalation.

FIG. 7 illustrates an air flow diagram within the first example implementation of the recovery and collection assembly 100 during a user exhalation. In FIG. 7, the reference numerals have been removed to aiding visualization of the airflow 15. As illustrated, the airflow 15 travels from the atomized material inhalation device 7(not illustrated in FIG. 7, illustrated and discussed in greater detail below) into the recovery and collection assembly 100 through the joint member 1. The airflow 15 then travels from the joint member 1 upward through the input tube 3 and out the upper end 13 into the chamber formed by the tubular sidewall 5. The airflow 15 then travels downward through the chamber formed by the tubular sidewall 5 and out through the openings 4 formed in the bottom of the end piece 2.

Figure 8:
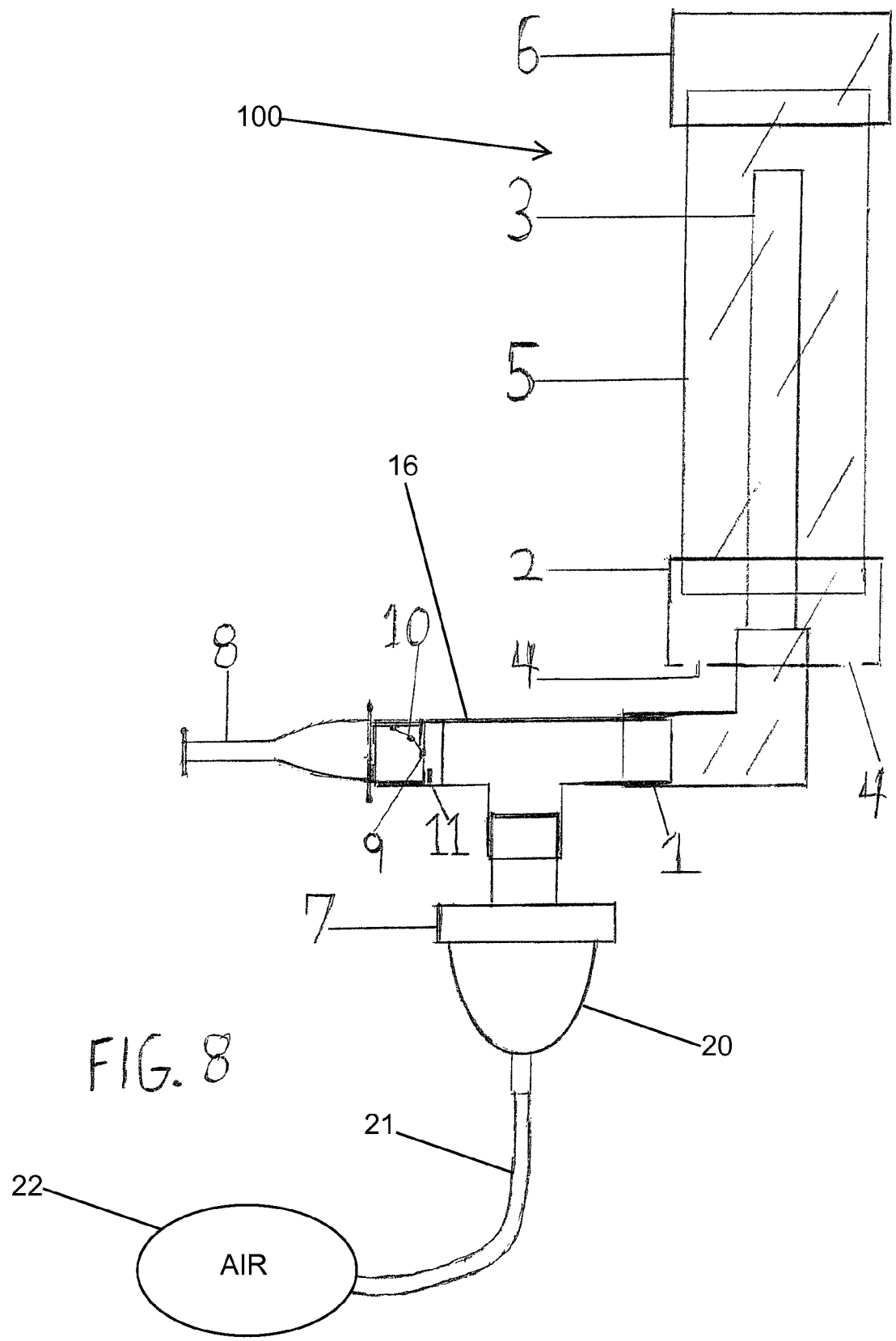
FIG. 8 illustrates a side view of the first example implementation of the recovery and collection assembly connected to a nebulizer and check gate mouthpiece.

FIG. 8 illustrates a side view of the first example implementation of the recovery and collection assembly 100 connected to an atomized material inhalation device 7 and check gate mouthpiece 8. As illustrated, a T-joint 16 is attached to the joint member 1 of the recovery and collection assembly 100. The T-joint 16 has a branched structure and connects to an atomized material inhalation device (e.g. a nebulizer) 7. A check gate mouthpiece 8 is also connected to the T-joint 16.

The check gate mouthpiece 8 may include a check gate valve 9 formed with by a valve member 11 and a biasing member 10 configured to hold the valve member 11 in a closed position. The check gate mouthpiece 8 is discussed in greater detail below with respect to FIGS. 13 and 14.

The atomized material inhalation device 7 is not particularly limited or limited to the configuration illustrated herein and may be any atomized material inhalation device that may be apparent to a person of ordinary skill in the art. As the structure and operation of an atomized material inhalation device 7 is not particularly limited a detailed discussion of the structure and operation thereof is omitted. Generally, an atomized material inhalation device 7 includes a material chamber 20 connected by a flow passage 21 to an air source 22 such as an oxygen cylinder, a respirator, ventilator, or any other air source that may be apparent to a person of ordinary skill in the art. The air source 22 provides a volume of air, which passes through a portion of material to be atomized in the material chamber 20 causing the material to be dispersed and atomized. In the example implementation illustrated in FIG. 8, the atomized material would pass out of the atomized material inhalation device 7 into the T-joint 16, where the atomized material can be inhaled by a user through the check gate mouthpiece 8. When the user exhales any excess atomized material can be blown into the chamber formed by the tubular sidewall 5 via the airflow 15 illustrated in FIG. 7 where it can be held until a subsequent inhalation. During a subsequent inhalation the excess atomized material within the chamber formed by the tubular sidewall 5 can be drawn back into the T-joint 16 by the airflow 15 illustrated in FIG. 6 and inhaled by the user.

Various aspects and features of example implementations of a recovery and collection assembly 100 have been discussed with reference to FIGS. 1-8 above. However, example implementations of the present application are not limited to aspects and features illustrated in FIGS. 1-8.

FIGS. 9-12 illustrate a second example implementation of a recovery and collection assembly 200. Aspects and features of the second example implementation may be similar to the aspects and features of the first example implementation discussed above and similar reference numerals may be used to identify similar features. FIG. 9 illustrates a side view of a second example implementation of the recovery and collection assembly 200. This second example implementation of the recovery and collection assembly 200 also includes an outer tubular housing formed by a tubular sidewall 5 and a pair of end caps or end pieces 2, 6 attach at opposite ends of the tubular sidewall 5. As illustrated, the end pieces 2, 6 may slide over the ends of the tubular sidewall 5 to form a chamber within the tubular sidewall 5. However, example implementations of the present application are not limited this configuration and may be formed by the end pieces 2, 6 being inserted into the tubular sidewall 5 to form the chamber, or may simply be attached to the end via various attachment mechanisms (such as welding, adhesive, mechanical interface, etc.) as may be apparent to a person of ordinary skill in the art. For reference purposes the chamber formed within the tubular sidewall 5 may be referred to herein as the outer chamber.

Additionally, the recovery and collection assembly 200 also includes a side flow port 12 extending from the tubular sidewall 5. The side flow port 12 may fluidly connect the interior of the chamber formed by the tubular sidewall 5 with the area surrounding the recovery and collection assembly 200. Further, as discussed in greater detail below, a check gate mouthpiece 8 may be attached to the flow port 12 as illustrated in all FIG. 10. In some example implementations, the side flow port 12 may have a circular cross-section. However, example implementations of the recovery and collection assembly 200 are not limited to this configuration and the flow port 12 may have other cross-sectional configurations as may be apparent to a person of ordinary skill in the art.

In some example implementations, the end pieces 2, 6 may be sealed to the tubular sidewall 5 by one or more of a gasket, an adhesive, a caulking compound, or any other sealing mechanism as may be apparent to a person of ordinary skill in the art to prevent any liquid or gas from leaking out. Further, the end pieces 2, 6 and tubular sidewall 5 may be formed from one or more of a plastic material, a composite material, a resin material, a ceramic material, a glass material, a metallic material, a nonmetallic material, or any other material as may be apparent to a person of ordinary skill in the art.

One end piece 2 may be formed with one or more openings 4 extending there through to allow fluid communications between the area surrounding the recovery and collection assembly 200 and the outer chamber formed within the tubular sidewall 5. The other end piece 6 may be formed with no openings or passageways to block any fluid communication between the area surrounding the recovery and collection assembly 200 and the outer chamber formed within the tubular sidewall 5.

Further, an input tube 3 may be inserted or penetrated through the end piece 2. The input tube 3 may have a first end 13 located within the outer chamber formed by the tubular sidewall 5 and a second end 14 located outside of the outer chamber formed by the tubular sidewall 5. Further, the second end 14 may be attached to a joint member 1, which may be configured to attach to an atomized material inhalation device 7(e.g. a nebulizer) as discussed in greater detail below. In some example implementations the joint member 1 may be a linear joint as illustrated. However, example implementations the present application are not limited to this configuration and may have other configurations as may be apparent to a person of ordinary skill in the art.

In some example implementations, the input tube 3 may be sealed to the end piece 2 by one or more of a gasket, an adhesive, a caulking compound, or any other sealing mechanism as may be apparent to a person of ordinary skill in the art to prevent any liquid or gas from leaking out. Additionally, the joint member 1 may also be sealed to the second end 14 of the input tube 3 using similar sealing mechanisms to those discussed above. The input tube 3 and the joint member 1 may be formed from one or more of a plastic material, a composite material, a resin material, a ceramic material, a glass material, a metallic material, a nonmetallic material, or any other material as may be apparent to a person of ordinary skill in the art.

As illustrated, during operation of some example implementations, the recovery and collection assembly 200 may be oriented such that the end piece 6 is an upper end piece 6 and the end piece 2 is a lower end piece 2 as illustrated in these figures. In such example implementations, the openings 4 are formed in the bottom surface of the lower end piece 2 (end piece). Additionally, the input tube 3 and the joint member 1 may also be inserted through the bottom surface of the lower end piece 2 as illustrated.

Additionally, the first end 13 of the input tube 3 may be positioned so that it is in an upper half of the chamber formed by the tubular sidewall 5. As discussed in greater detail below the placement of the first end 13 in an upper half of the chamber may affect retention of atomized material within the recovery and collection assembly. In some example implementations, the joint member 1 may be a linear joint oriented to provide a vertical opening in downward direction. However, example implementations of the present application are not limited this configuration and may take on alternate configurations as may be apparent to a person of ordinary skill in the art.

Figure 9:
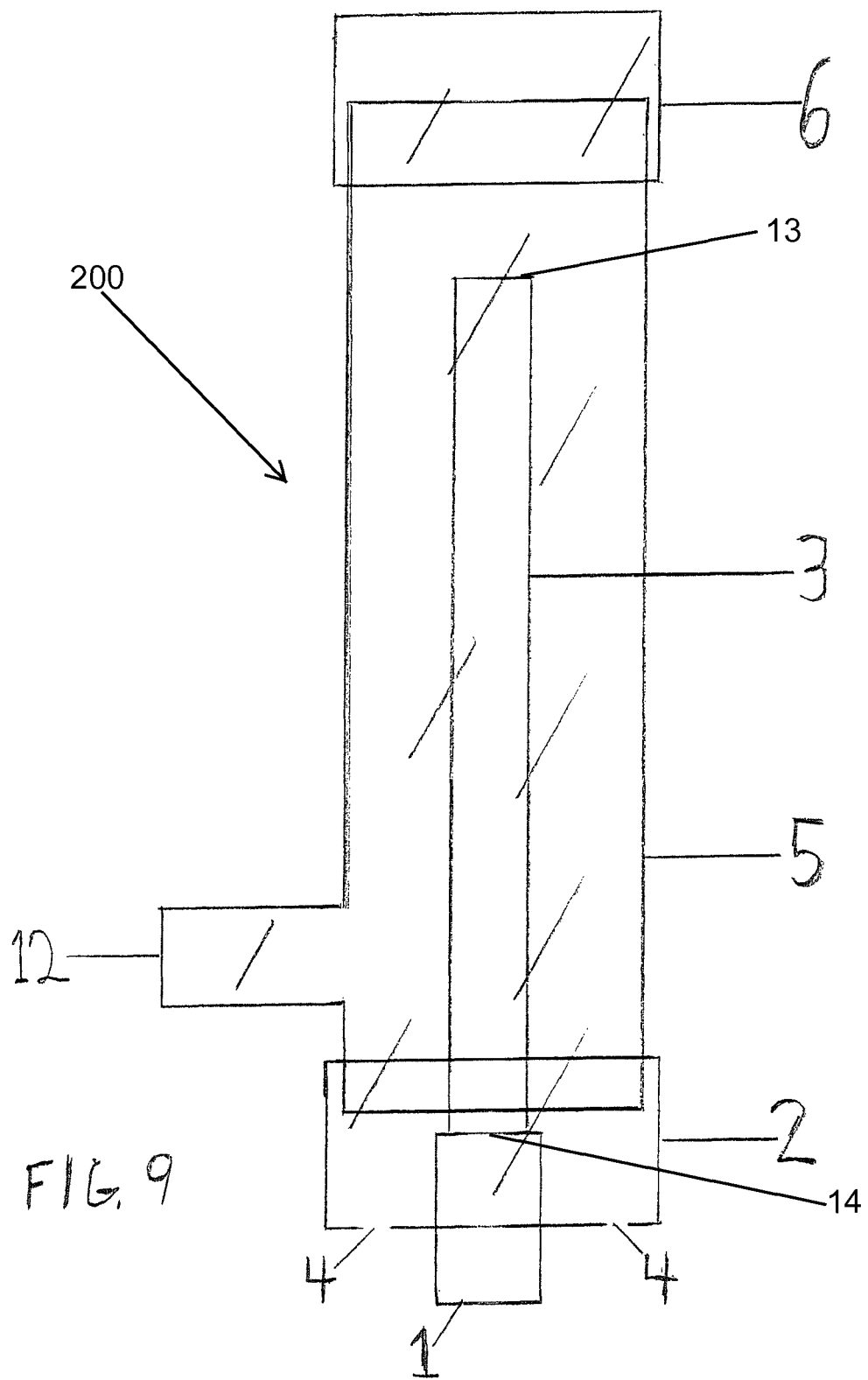
FIG. 9 illustrates a side view of a second example implementation of the recovery and collection assembly.

Though not illustrated in FIG. 9, the recovery and collection assembly 200 may be formed with a generally circular cross-section, similar to the cross-section of the recovery and collection assembly 100 in FIGS. 5A and 5B above. More specifically, the tubular sidewall 5, and the end pieces 2, 6 may have circular cross-sections. Further, the input tube 3 may also have a circular cross-section and be positioned at an approximate radial center of the end pieces 2, 6 and the tubular sidewall 5.

Figure 10:
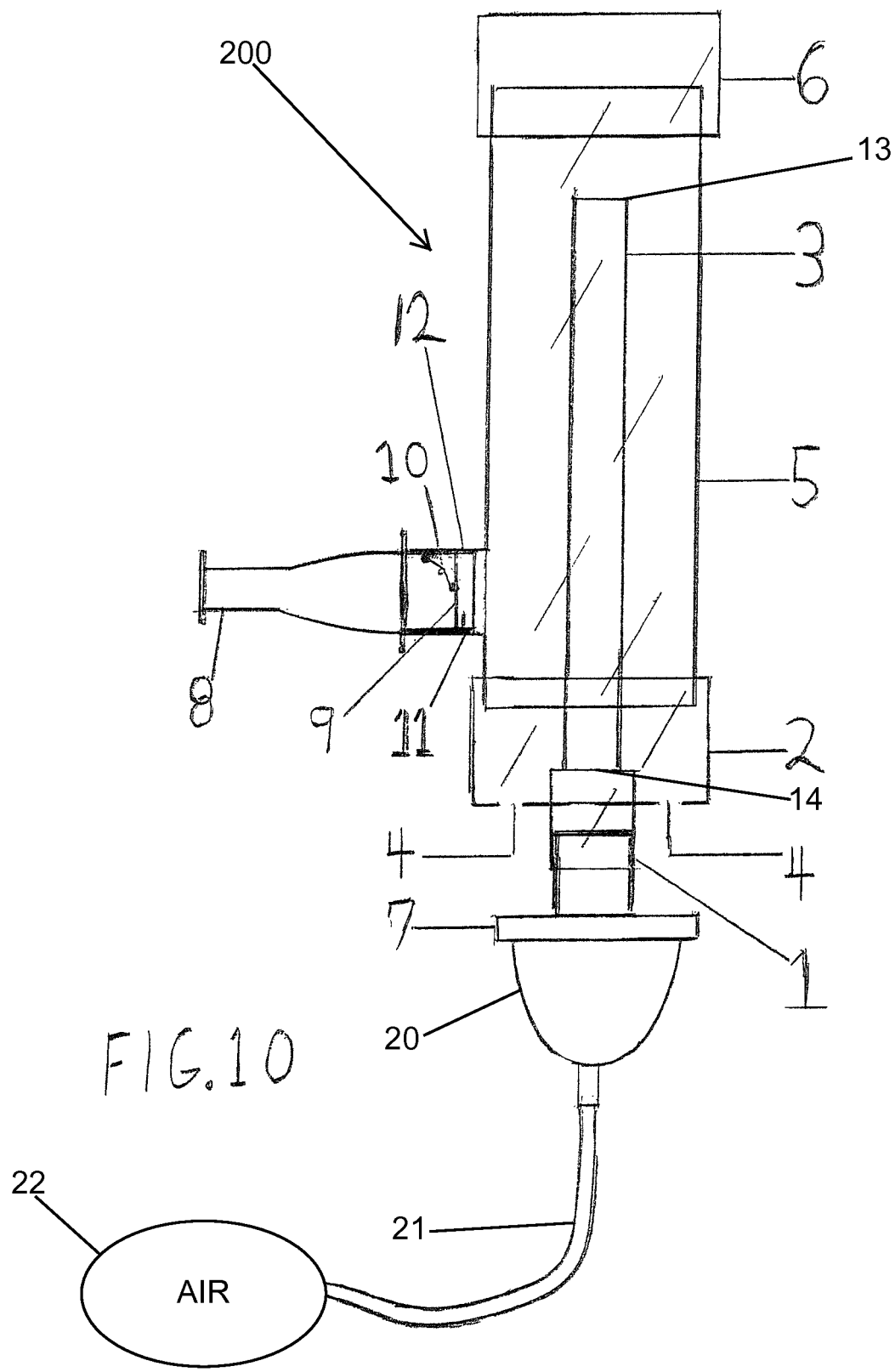
FIG. 10 illustrates a side view of the second example implementation of the recovery and collection assembly connected to a nebulizer and check gate mouthpiece.

FIG. 10 illustrates a side view of the second example implementation of the recovery and collection assembly 200 connected to an atomized material inhalation device 7 and check gate mouthpiece 8. As illustrated, an atomized material inhalation device (e.g. a nebulizer) 7 is attached directly to the lower end of the joint member 1. Further, a check gate mouthpiece 8 is attached to side flow port 12 extending from the tubular sidewall 5.

As illustrated, the check gate mouthpiece 8 may include a check gate valve 9 formed with by a valve member 11 and a biasing member 10 configured to hold the valve member 11 in a closed position. The check gate mouthpiece 8 is discussed in greater detail below with respect to FIGS. 13 and 14.

The atomized material inhalation device 7 is not particularly limited or limited to the configuration illustrated herein and may be any atomized material inhalation device that may be apparent to a person of ordinary skill in the art. As the structure and operation of an atomized material inhalation device 7 is not particularly limited a detailed discussion of the structure and operation thereof is omitted. Generally, an atomized material inhalation device 7 includes a material chamber 20 connected by a flow passage 21 to an air source 22 such as an oxygen cylinder, a respirator, ventilator, or any other air source that may be apparent to a person of ordinary skill in the art. The air source 22 provides a volume of air, which passes through a portion of material to be atomized in the material chamber 20 causing the material to be dispersed and atomized. Additionally, the atomized material provided by the atomized material inhalation device 7 is also not particularly limited and may include medicines and other compounds capable of being delivered to a user via an atomized material inhalation device 7 (e.g. a nebulizer). For example, the atomized material making may include Leukine®, Albuterol, Mucomyst®, Tobramycin, Levalbuterol, or any other atomized material that may be apparent to a person of ordinary skill in the art.

In the example implementation illustrated in FIG. 10, the atomized material would pass out of the atomized material inhalation device 7 into the joint member 1, where the atomized material would flow upward through the input tube 3 and into the chamber formed by the tubular sidewall 5. When the user is not inhaling, the valve member 11 remains in a closed position and the atomized material remain in the chamber formed by the tubular sidewall 5 (via the airflow 17 illustrated in FIG. 11 below) where it can be held until a subsequent inhalation. When a user inhales, the valve member 11 opens and the atomized material within the chamber formed by the tubular sidewall 5 can be drawn through the side flow port 12, into the mouth piece 8 (by the airflow 17 and the airflow 18 illustrated in FIG. 12, below) and inhaled by the user.

Figure 11:
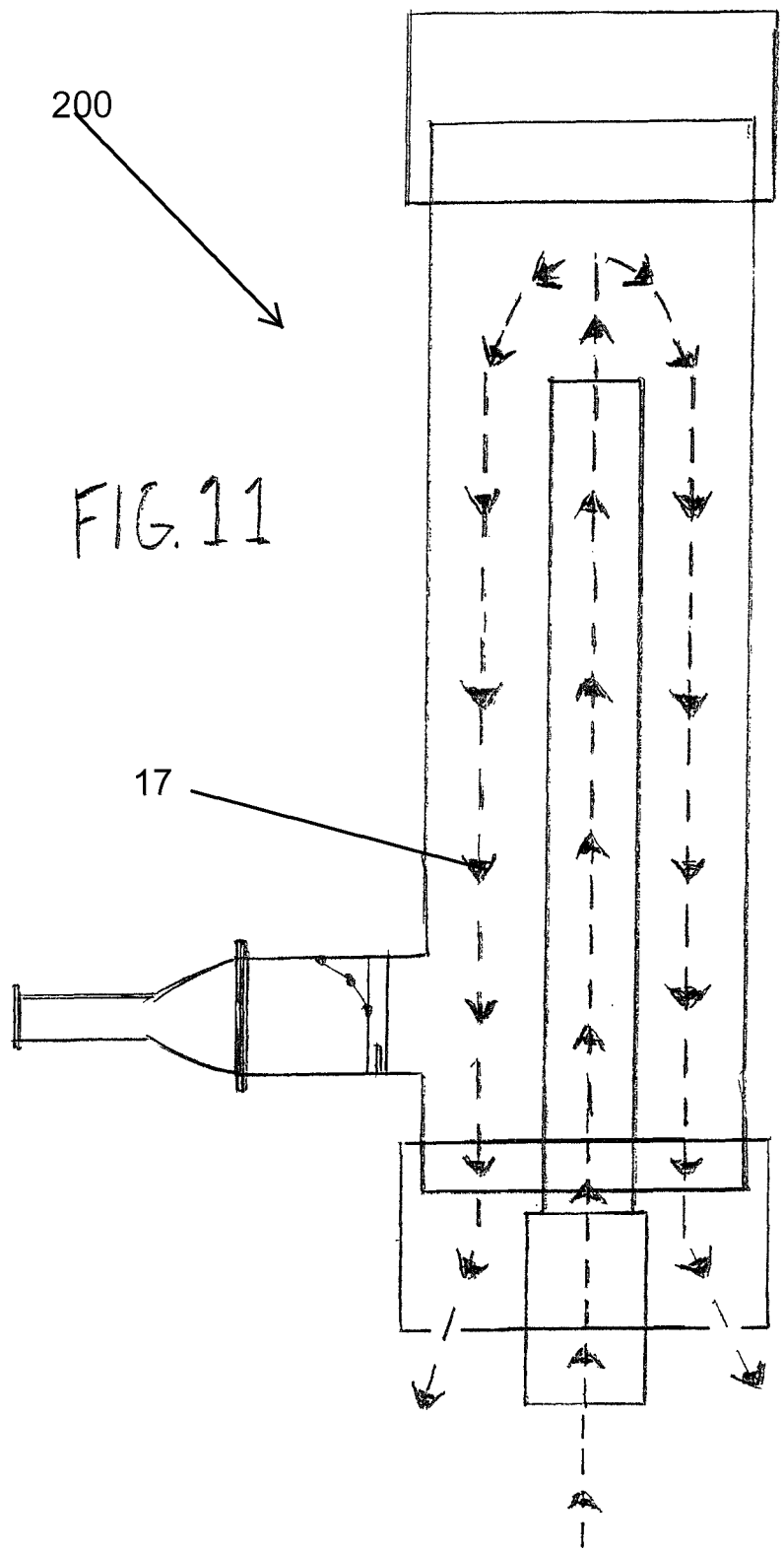
FIG. 11 illustrates an air flow diagram within the second example implementation of the recovery and collection assembly during a user inhalation.

FIG. 11 illustrates an air flow diagram within the second example implementation of the recovery and collection assembly 200 before a user inhalation phase. In FIG. 11, the reference numerals have been removed to aiding visualization of the airflow 17. As illustrated, the airflow 17 travels from the joint member 1 through the input tube 3, out the upper end 13 and into the chamber formed by the tubular sidewall 5. The airflow 17 then travels downward through the chamber formed by the tubular sidewall 5 and out the openings 4 formed in the lower end piece 2.

Figure 12:
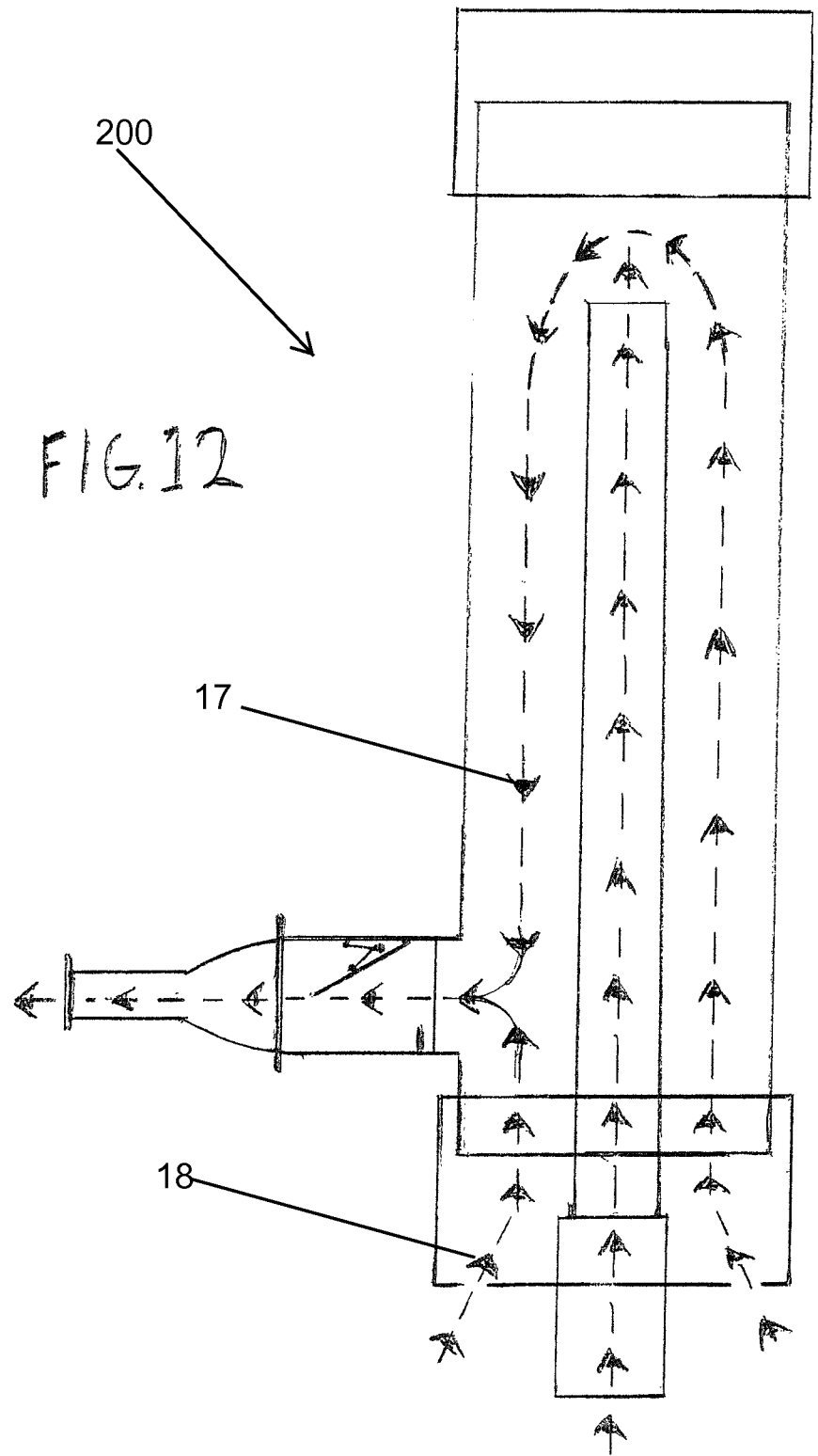
FIG. 12 illustrates an air flow diagram within the second example implementation of the recovery and collection assembly during a user exhalation.

FIG. 12 illustrates an air flow diagram within the second example implementation of the recovery and collection assembly 200 during a user inhalation. In FIG. 12, the reference numerals have been removed to aiding visualization of two airflows 17 and 18. As illustrated, the first airflow 17 travels from the joint member 1 through the input tube 3, out the upper end 13 and into the chamber formed by the tubular sidewall 5. The first airflow 17 then travels downward through the chamber formed by the tubular sidewall 5, through the side flow port 12 and into the mouth piece 8 to be inhaled by the user. Further, a second airflow 18 travels upward from the openings 4 formed in the lower end piece 2 through the side flow port 12 and into the mouth piece 8 to also be inhaled by the user. In some example implementations, the first airflow 17 may carry the atomized material from the atomized material inhalation device (e.g. Nebulizer) 7 through the recovery and collection assembly 200 to the mouthpiece 8. Further, the second airflow 18 may bring additional atmospheric air into the mouthpiece 8.

Figure 13:
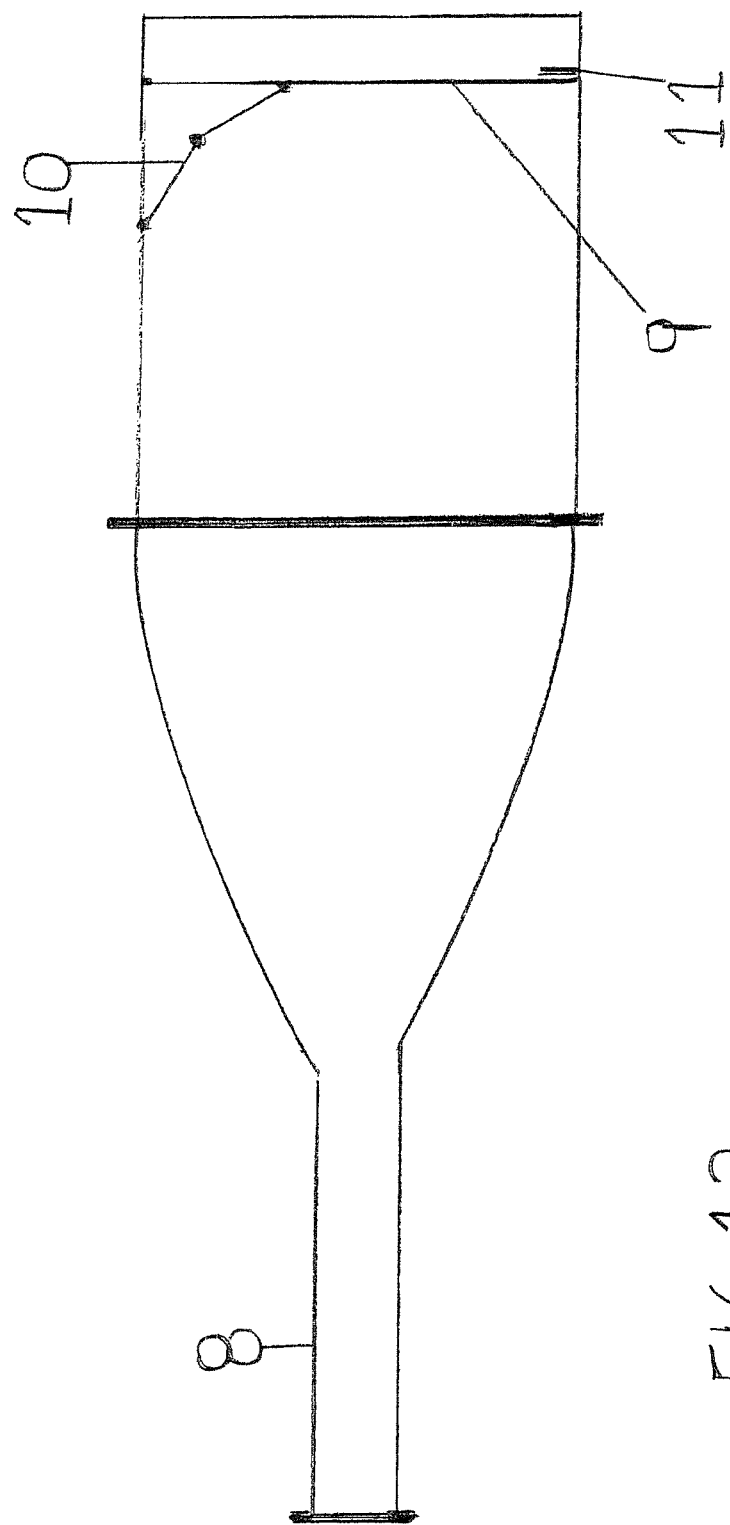
FIG. 13 illustrates a side view of an example implementation of a check gate mouthpiece in a closed position.
Figure 14:
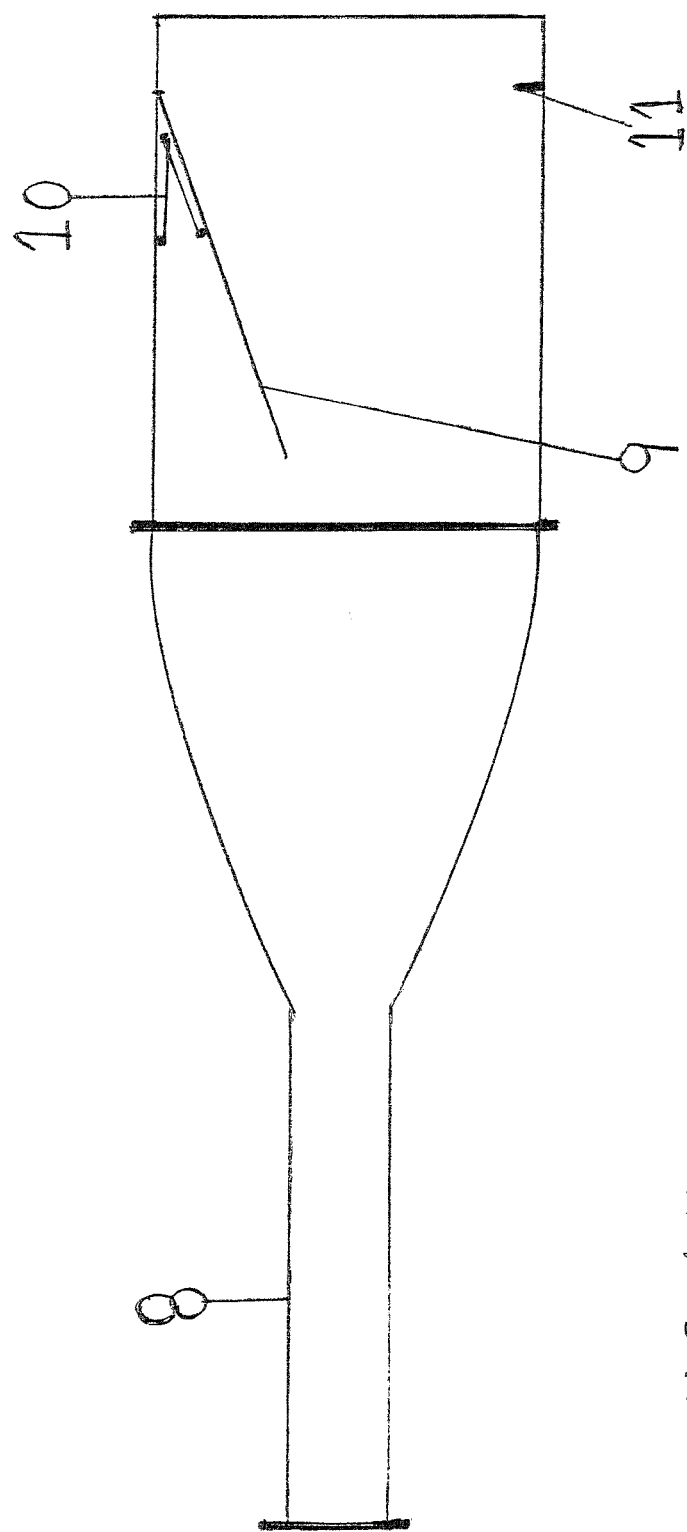
FIG. 14 illustrates a side view of an example implementation of a check gate mouthpiece in an opened position.

FIG. 13 illustrates a side view of an example implementation of a check gate mouthpiece 8 in a closed position and FIG. 14 illustrates a side view of the example implementation of the check gate mouthpiece 8 in an opened position. As illustrated, the check gate mouthpiece 8 includes a check gate valve 9 which selectively blocks fluid flow through the check gate mouthpiece 8. The check gate valve 9 includes a valve member 11 and a biasing member 10. The valve member 11 is configured to be operable between a closed position (illustrated in FIG. 13) and an open position (illustrated in FIG. 14). The valve member 11 may be configured to block fluid flow into the check gate mouthpiece 8 in the closed position.

The biasing member 10 may provide a biasing force to the valve member 11 and urge the valve member 11 toward the closed position (illustrated in FIG. 13). Further, the valve member 11 may move into an open position (illustrated in FIG. 14) in response to an external force, such as a negative pressure generated by a user inhalation through the check gate mouthpiece 8.

In the example implementation illustrated in FIGS. 13 and 14, the valve member 11 may be a hinged member configured to rotate about a fixed point between the closed position of FIG. 13 and the open position of FIG. 14. Further, the biasing member 10 may be a torsion spring configured to provide a torque to the valve member 11 to urge the valve member 11 toward the closed position of FIG. 13. However, example implementations of the present application are not limited to this configuration and may have alternate configurations as may be apparent to a person of ordinary skill in the art. For example, the valve member 11 may be a linear valve or ball valve and the biasing member 10 may be a linear spring, for example.

Example implementations of the present application may allow a cost savings and/or allow more effective treatment by collecting and recovering atomized materials during nebulizer treatments. For example, the average time between the inhalation and exhalation of a person is approximately seven seconds. In this seven second span, an example implementation of a recovery and collection assembly may allow for the recovery and concentration of atomized materials in amounts that will remain are available to the user during a subsequent inhalation. When the nebulizer is used alone, the atomized material provided by the nebulizer may be lost to the atmosphere between the inhalations by the user. These losses could be up to 50% of the atomized material provided by the nebulizer. By using a recovery and collection assembly according to an example implementation of the present application, the atomized material losses to the atmosphere may be reduced from 50% to 20% depending on the health and lung strength of the user.

As discussed above, some treatments provided via nebulizers can cost $250 or more per dose, with a patient receiving multiple doses every day over the course of months or years. A recovery and collection assembly according to an example implementation of the present application may allow a user to receive more atomized materials per dose with improved efficiency, less waste, and reduced costs. Though one or more of these positive outcomes may be achieved through the use of a recovery and collection assembly according to an example implementation of the present application, example implementations of the present application need not achieve these or any other positive outcomes and should not limit the scope of the claims provided here with.

While certain example implementations have been described, these example implementations have been presented by way of example only, and are not intended to limit the scope of the protection. Indeed, the novel apparatuses described herein may be embodied in a variety of other forms. Furthermore, various omissions, substitutions and changes in the form of the systems described herein may be made without departing from the spirit of the protection. The accompanying claims and their equivalents are intended to cover such forms or modifications as would fall within the scope and spirit of the protection.

What is claimed is:

1. A recovery and collection assembly for an atomized material inhalation device, the recovery and collection assembly comprising:
    an outer tubular housing, the outer tubular housing including
    a sidewall defining an outer chamber;
    an upper end piece attached to an upper end of the sidewall; and
    a lower end piece attached to a lower end of the sidewall, the lower end piece having at least one air flow opening allowing fluid communication between an interior of the outer chamber and an atmosphere surrounding the outer tubular housing;
    an input tube extending through the lower end piece, the input tube having a first end in fluid communication with the atomized material inhalation device, and a second end disposed in an upper half of the outer chamber and in fluid communication with the outer chamber, the input tube defining an inner chamber;
    a joint member attached to the first end of the input tube, the joint member defining a connection port configured to fluidly communicate with the atomized material inhalation device; and
    a mouthpiece attached to the joint member and in fluid communication with the outer chamber, the mouthpiece having a gate valve, which selectively controls fluid communication between the mouthpiece and the outer chamber.

2. The recovery and collection assembly according to claim 1, wherein the gate valve comprises a hinged member and a biasing member configured to bias the hinged member toward a closed position.

3. The recovery and collection assembly according to claim 1, wherein the connection port is disposed between the mouthpiece and the first end of the input tube.

4. The recovery and collection assembly according to claim 1, wherein the sidewall further comprises a flow port allowing fluid communication between the interior of the outer chamber and the atmosphere surrounding the outer tubular housing.

5. The recovery and collection assembly according to claim 4, further comprising a mouthpiece attached to the flow port and in fluid communication with the outer chamber, the mouthpiece has a gate valve selectively controlling communication between the mouthpiece and the outer chamber.

6. The recovery and collection assembly according to claim 5, wherein the gate valve comprises a hinged member and a biasing member configured to bias the hinged member toward a closed position.

7. An atomized material inhalation device comprising:
    a material chamber;
    an air source;
    a flow passage connecting the air source to the material chamber; and
    a recovery and collection assembly, the recovery and collection assembly comprising:
    an outer tubular housing, the outer tubular housing including
    a sidewall defining an outer chamber;
    an upper end piece attached to an upper end of the sidewall; and
    a lower end piece attached to a lower end of the sidewall, the lower end piece having at least one air flow opening allowing fluid communication between an interior of the outer chamber and an atmosphere surrounding the outer tubular housing;
    an input tube extending through the lower end piece, the input tube having a first end in fluid communication with the material chamber, and a second end disposed in an upper half of the outer chamber and in fluid communication with the outer chamber, the input tube defining an inner chamber;
    a joint member attached to the first end of the input tube, the joint member defining a connection port configured to fluidly communicate with the atomized material inhalation device; and a mouthpiece attached to the joint member and in fluid communication with the outer chamber, the mouthpiece having a gate valve, which selectively controls fluid communication between the mouthpiece and the outer chamber.

8. The atomized material inhalation device according to claim 7, wherein the gate valve comprises a hinged member and a biasing member configured to bias the hinged member toward a closed position.

9. The atomized material inhalation device according to claim 7, wherein the connection port is disposed between the mouthpiece and the first end of the input tube.

10. The atomized material inhalation device according to claim 7, wherein the sidewall further comprises a flow port allowing fluid communication between the interior of the outer chamber and the atmosphere surrounding the outer tubular housing.

11. The atomized material inhalation device according to claim 10, further comprising a mouthpiece attached to the flow port and in fluid communication with the outer chamber, the mouthpiece has a gate valve selectively controlling communication between the mouthpiece and the outer chamber.

12. The atomized material inhalation device according to claim 11, wherein the gate valve comprises a hinged member and a biasing member configured to bias the hinged member toward a closed position.

\* \* \* \* \*